US009194874B2

(12) United States Patent
Irie et al.

(10) Patent No.: US 9,194,874 B2
(45) Date of Patent: Nov. 24, 2015

(54) TEST METHOD FOR MALE FERTILITY BY DETECTING A MUTATION IN THE PGAM4 GENE (75) Inventors: Shinji Irie, Tokyo (JP); Akira Tsujimura, Osaka (JP); Yasushi Miyagawa, Osaka (JP); Hiromitsu Tanaka, Sasebo (JP)

(73) Assignees: TOPPAN PRINTING CO., LTD., Tokyo (JP); OSAKA UNIVERSITY, Osaka (JP); KYUSHU BUNKA GAKUEN SCHOOL FOUNDATION, Nagasaki (JP)

( * ) Notice: Subject to any disclaimer, the term of this patent is extended or adjusted under 35 U.S.C. 154(b) by 1101 days.

(21) Appl. No.: 13/256,860

(22) PCT Filed: Mar. 15, 2010

(86) PCT No.: PCT/JP2010/001850
§ 371 (c)(1),
(2), (4) Date: Sep. 15, 2011

(87) PCT Pub. No.: WO2010/106788
PCT Pub. Date: Sep. 23, 2010

(65) Prior Publication Data
US 2012/0116243 A1  May 10, 2012

(30) Foreign Application Priority Data
Mar. 17, 2009  (JP) ................ P2009-065110

(51) Int. Cl.
C12Q 1/68    (2006.01)
C07H 21/02   (2006.01)
C07H 21/04   (2006.01)
G01N 33/68   (2006.01)

(52) U.S. Cl.
CPC ............ *G01N 33/689* (2013.01); *C12Q 1/6883* (2013.01); *C12Q 2600/156* (2013.01); *C12Q 2600/158* (2013.01); *G01N 2333/99* (2013.01)

(58) Field of Classification Search
None
See application file for complete search history.

(56) References Cited

FOREIGN PATENT DOCUMENTS

| JP | 7-258299 | 10/1995 |
|---|---|---|
| JP | 2007-089409 | 4/2007 |
| JP | 2008-237114 | 10/2007 |
| JP | 2008-067649 | 3/2008 |
| JP | 4229973 | 2/2009 |
| JP | 2009-065882 | 4/2009 |
| JP | 4276691 | 6/2009 |

OTHER PUBLICATIONS

Jin et al. Systems Biology Reproductive Medicine. 2013. 59: 179-183.*
Hirschhorn et al. (Genetics in Medicine. 2002. 4(2): 45-61.*
Hattersley et al. The Lancet. 2005. 366: 1315-1323.*
Lucentini et al. The Scientist (2004) vol. 18, p. 20.*
Extended European Search Report mailed Jan. 17, 2013 for corresponding European Application No. 10753285.5.
Cristina Broceño et al., "The muscle-specific phosphoglycerate mutase gene is specifically expressed in testis during spermatogenesis", European Journal of Biochemistry, vol. 227, No. 3, 1995, XP002689121, ISSN:0014-2956.
O. Musumeci et al., "Two novel mutations associated with muscle phosphoglycerate mustase (PGAM) deficiency", Neuromuscular Disorders, Pergamon Press, GB, vol. 18, No. 9-10, Oct. 1, 2008, p. 829, XP023907282.
Hidenobu Okuda et al., "A Single Nucleotide Polymorphism within the Novel Sex-Linked Testis-Specific Retrotransposed PGAM4 Gene Influences Human Male Fertility", PLOS ONE, vol. 7, No. 5, May 2012, XP002689122.
International Search Report of PCT/JP2010/001850 mailed on Apr. 13, 2010.
Fundele et al., "Developmental Activation of Phosphoglycerate Mutase-2 in the Testis of the Mouse", Developmental Biology vol. 124, pp. 562-566 (1987).
Zhang et al., "Mouse phosphoglycerate mutase M and B isozymes: cDNA cloning, enzyme activity assay and mapping", Gene vol. 264 (2001) pp. 273-279.
Sakoda et al., "Isolation of a cDNA Encoding and B Isozyme of Human Phosphoglycerate Mutase (PGAM) and Characterization of the PGAM Gene Family", The Journal of Biological Chemistry (1988) vol. 263, No. 32, pp. 16899-16905.
"Gene Symbol Report: PGAM4", Apr. 25, 2005, Human Genome Organization, <URL:http://www.genenames.org/data/hgnc_data.php?hgnc_id=21731>.
McCarrey et al., "Human testis-specific PGK gene lacks introns and possesses characteristics of a processed gene", Nature vol. 326 (1987), pp. 501-505.

(Continued)

*Primary Examiner* — Carla Myers (57) ABSTRACT

An object of the present invention is to provide a test/diagnosis method for fertility which allows the estimation of the possibility of leading to pregnancy based on the ability of sperm to fuse with an egg and the identification of a cause of infertility; and a polynucleotide and a fertility testing kit which are used in the method. The present invention provides a test/diagnosis method for fertility, including a detection step of detecting on a biological sample taken from a human body, the presence or absence of a deletion or mutation in the human PGAM4 gene; a polynucleotide consisting of the base sequence of the human wild-type PGAM4 gene or the base sequence of the translation region of the gene, wherein the polynucleotide consists of a base sequence of 10-100 consecutive bases containing a mutated site of a single base substitution mutation having a high correlation with fertility; and a test kit for fertility comprising a reagent for detecting the presence or absence of a deletion or mutation in the human PGAM4 gene.

2 Claims, 1 Drawing Sheet (56) References Cited

OTHER PUBLICATIONS

Dahl et al., "A Testis-Specific Form of the Human Pyruvate Dehydrogenase E1*a* Subunit is Coded for by an Intronless Gene on Chromosome 4", GENOMICS8 (1990), pp. 225-232.

Dierick H.A. et al., "A phosphoglycerate mutase brain isoform (PGAM1) pseudogene is localized within the human Menkes disease gene (ATP7A)", Gene, 1997, vol. 198, p. 37-41.

Betrán E. et al., "Evolution of the Phosphoglycerate mutase Processed Gene in Human and Chimpanzee Revealing the Origin of a New Primate Gene", Mol. Biol. Evol., 2002, vol. 19, p. 654-663.

Tanaka, Hiromitsu et al., "Seiso Seishoku Saibo Tokuiteki Idenshi no single-nucleotide polymorphism (SNP) Kaiseki", Proceedings of the Japan Society of Andrology the Annual Meeting, 2007, pp. 152 to 153.

Miyagawa, Yasushi et al., "Dansei Funinsho Kanja ni Okeru Seiso Seishoku Saibo Tokuiteki Idenshi SNP Kaiseki to sono Rinsho Oyo", Proceedings of the Japan Society of Andrology the Annual Meeting, 2008, pp. 82 to 83.

Miyagawa, Yasushi et al., "Dansei Funinsho to Seishi Keisei Idenshi" (Male Infertility and Spermiogenic Genes), Proceedings of the Japanese Society of Animal Models for Human Diseases, 2004, vol. 20, pp. 29 to 34.

Tanaka, Hiromitsu et al., "Dansei Funinsho no Genin Idenshi no Dotei to Rinsho Oyo", Kosei Rodo Kagaku Kenkyuhi Hojokin Hito Genome Saisei Iryo to Kenkyu Jigyo Heisei 15 Nendo Sokatsu Kenkyu Hokokusho, 2004, pp. 19 to 22.

International Search Report mailed on Apr. 13, 2010 in corresponding International Patent Application PCT/JP2010/001850.

* cited by examiner

SEQUENCE LISTING

<160> NUMBER OF SEQ ID NOS: 7

<210> SEQ ID NO 1
<211> LENGTH: 765
<212> TYPE: DNA
<213> ORGANISM: Homo sapiens

<400> SEQUENCE: 1

```
atg gcc gcc tac aaa ctg gtg ctg atc cgg cac ggc gag agc aca tgg        48
Met Ala Ala Tyr Lys Leu Val Leu Ile Arg His Gly Glu Ser Thr Trp
1               5                   10                  15 aac ctg gag aac cgc ttc agc tgc tgg tac gac gcc gat ctg agc ccg        96
Asn Leu Glu Asn Arg Phe Ser Cys Trp Tyr Asp Ala Asp Leu Ser Pro
            20                  25                  30 gcg ggc cac gag gag gcg aag cgc ggc ggg cag gcg cta cga gat gct       144
Ala Gly His Glu Glu Ala Lys Arg Gly Gly Gln Ala Leu Arg Asp Ala
        35                  40                  45 ggc tat gag ttt gac atc tgc ctc acc tca gtg cag aag aga gtg atc       192
Gly Tyr Glu Phe Asp Ile Cys Leu Thr Ser Val Gln Lys Arg Val Ile
    50                  55                  60 cgg acc ctc tgg aca gtg cta gat gcc att gat cag atg tgg ctg cca       240
Arg Thr Leu Trp Thr Val Leu Asp Ala Ile Asp Gln Met Trp Leu Pro
65                  70                  75                  80 gtg gtg agg act tgg cgc ctc aat gag cgg cac tat ggg ggt cta acc       288
Val Val Arg Thr Trp Arg Leu Asn Glu Arg His Tyr Gly Gly Leu Thr
                85                  90                  95 ggt ctc aat aaa gca gaa act gct gca aag cat ggt gag gcc cag gtg       336
Gly Leu Asn Lys Ala Glu Thr Ala Ala Lys His Gly Glu Ala Gln Val
            100                 105                 110 aag atc tgg agg cgc tcc tat gat gtc cca cca cct ccg atg gag ccc       384
Lys Ile Trp Arg Arg Ser Tyr Asp Val Pro Pro Pro Pro Met Glu Pro
        115                 120                 125
```

```
gac cat cct ttc tac agc aac atc agt aag gat cgc agg tat gca gac      432
Asp His Pro Phe Tyr Ser Asn Ile Ser Lys Asp Arg Arg Tyr Ala Asp
    130                 135                 140 ctc aca gaa gat cag cta ccc tcc tat gag agt ccg aag gat act att      480
Leu Thr Glu Asp Gln Leu Pro Ser Tyr Glu Ser Pro Lys Asp Thr Ile
145                 150                 155                 160 gcc aga gct ctg ccc ttc tgg aat gaa gaa ata gtt ccc cag atc aag      528
Ala Arg Ala Leu Pro Phe Trp Asn Glu Glu Ile Val Pro Gln Ile Lys
                165                 170                 175 gag ggg aaa cgt gta ctg att gca gcc cat ggc aac agc ctc cag ggc      576
Glu Gly Lys Arg Val Leu Ile Ala Ala His Gly Asn Ser Leu Gln Gly
            180                 185                 190 att gcc aag cat gtg gag ggt ctc tct gaa gag gct atc atg gag ctg      624
Ile Ala Lys His Val Glu Gly Leu Ser Glu Glu Ala Ile Met Glu Leu
        195                 200                 205 aac ctg ccg act ggt att ccc atc gtc tat gaa ttg gac aag aac ttg      672
Asn Leu Pro Thr Gly Ile Pro Ile Val Tyr Glu Leu Asp Lys Asn Leu
    210                 215                 220 aag cct atc aag ccc atg cag ttt ctg ggg gat gaa gag acg gtg tgc      720
Lys Pro Ile Lys Pro Met Gln Phe Leu Gly Asp Glu Glu Thr Val Cys
225                 230                 235                 240 aaa gcc ata gaa gct gtg gct gcc cag ggc aag gcc aag aag tga          765
Lys Ala Ile Glu Ala Val Ala Ala Gln Gly Lys Ala Lys Lys
                245                 250

<210> SEQ ID NO 2
<211> LENGTH: 254
<212> TYPE: PRT
<213> ORGANISM: Homo sapiens

<400> SEQUENCE: 2

Met Ala Ala Tyr Lys Leu Val Leu Ile Arg His Gly Glu Ser Thr Trp
1               5                   10                  15

Asn Leu Glu Asn Arg Phe Ser Cys Trp Tyr Asp Ala Asp Leu Ser Pro
            20                  25                  30

Ala Gly His Glu Glu Ala Lys Arg Gly Gly Gln Ala Leu Arg Asp Ala
        35                  40                  45

Gly Tyr Glu Phe Asp Ile Cys Leu Thr Ser Val Gln Lys Arg Val Ile
    50                  55                  60

Arg Thr Leu Trp Thr Val Leu Asp Ala Ile Asp Gln Met Trp Leu Pro
65                  70                  75                  80

Val Val Arg Thr Trp Arg Leu Asn Glu Arg His Tyr Gly Gly Leu Thr
                85                  90                  95

Gly Leu Asn Lys Ala Glu Thr Ala Ala Lys His Gly Glu Ala Gln Val
            100                 105                 110

Lys Ile Trp Arg Arg Ser Tyr Asp Val Pro Pro Pro Met Glu Pro
        115                 120                 125

Asp His Pro Phe Tyr Ser Asn Ile Ser Lys Asp Arg Arg Tyr Ala Asp
    130                 135                 140

Leu Thr Glu Asp Gln Leu Pro Ser Tyr Glu Ser Pro Lys Asp Thr Ile
145                 150                 155                 160

Ala Arg Ala Leu Pro Phe Trp Asn Glu Glu Ile Val Pro Gln Ile Lys
                165                 170                 175

Glu Gly Lys Arg Val Leu Ile Ala Ala His Gly Asn Ser Leu Gln Gly
            180                 185                 190

Ile Ala Lys His Val Glu Gly Leu Ser Glu Glu Ala Ile Met Glu Leu
        195                 200                 205
```

```
Asn Leu Pro Thr Gly Ile Pro Ile Val Tyr Glu Leu Asp Lys Asn Leu
        210                 215                 220

Lys Pro Ile Lys Pro Met Gln Phe Leu Gly Asp Glu Glu Thr Val Cys
225                 230                 235                 240

Lys Ala Ile Glu Ala Val Ala Ala Gln Gly Lys Ala Lys Lys
                245                 250

<210> SEQ ID NO 3
<211> LENGTH: 201
<212> TYPE: DNA
<213> ORGANISM: Homo sapiens

<400> SEQUENCE: 3
tataaaaagt attgcagccc accgccatgg ccgcctacaa actggtgctg atccggcacg     60
gcgagagcac atggaacctg agaaccgct tcagctgctg gtacgacgcc gatctgagcc    120
cggcgggcca cgaggaggcg aagcgcggcg ggcaggcgct acgagatgct ggctatgagt    180
ttgacatctg cctcacctca g                                              201

<210> SEQ ID NO 4
<211> LENGTH: 201
<212> TYPE: DNA
<213> ORGANISM: Homo sapiens

<400> SEQUENCE: 4
agagcacatg gaacctggag aaccgcttca gctgctggta cgacgccgat ctgagcccgg     60
cgggccacga ggaggcgaag cgcggcgggc aggcgctacg agatgctggc tatgagtttg    120
acatctgcct cacctcagtg cagaagagag tgatccggac cctctggaca gtgctagatg    180
ccattgatca gatgtggctg c                                              201

<210> SEQ ID NO 5
<211> LENGTH: 201
<212> TYPE: DNA
<213> ORGANISM: Homo sapiens

<400> SEQUENCE: 5
gaagatcagc taccctccta tgagagtccg aaggatacta ttgccagagc tctgcccttc     60
tggaatgaag aaatagttcc ccagatcaag gaggggaaac gtgtactgat gcagcccat    120 ggcaacagcc tccagggcat tgccaagcat gtggagggtc tctctgaaga ggctatcatg    180
gagctgaacc tgccgactgg t                                              201

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Primer F.

<400> SEQUENCE: 6
gagtggttag ggaataaggg tggg                                            24

<210> SEQ ID NO 7
<211> LENGTH: 24
```

-continued

```
<212> TYPE: DNA
<213> ORGANISM: Artificial Sequence
<220> FEATURE:
<223> OTHER INFORMATION: Description of Artificial Sequence: Primer R.

<400> SEQUENCE: 7
agtgtgacat gtgcaggtgg gagg                                           24
```

TEST METHOD FOR MALE FERTILITY BY DETECTING A MUTATION IN THE PGAM4 GENE

CROSS-REFERENCE TO RELATED APPLICATIONS

This application is a national phase application, under 35 U.S.C. 371, of international application No. PCT/JP2010/001850, filed on Mar. 15, 2010, which claimed priority to Japanese Patent Application No. P2009-065110, filed on Mar. 17, 2009, the disclosures of which are incorporated herein by reference.

TECHNICAL FIELD

The present invention relates to techniques capable of estimation of the possibility of leading to pregnancy and identification of a cause of infertility. Specifically, the present invention relates to a method for detecting a deletion or mutation in a gene which has a correlation with the possibility of leading to pregnancy, thereby testing or diagnosing the possibility of leading to pregnancy, and to a kit, a polynucleotide, a polypeptide, and an antibody which can be employed in such a method.

BACKGROUND ART

Recently, problems related to a decreasing birthrate are frequently taken up, and various countermeasures have been tried in order to solve these problems. As countermeasures against a decreasing birthrate, it is obvious that it is important to give aid to couples who have no child due to infertility, while there is a strong request for developing effective treatments of infertility.

Infertility is caused at the same rate between men and women. However, because of the complexity of the mechanism of sperm formation, male infertility is not elucidated in many aspects, including its treatments, and there are unknown causes in many of the reproduction-associated problems, such as decreased number of human sperms and reduced reproductive potential. Although technical progress of In Vitro Fertilization (IVF) has become capable of conceiving and birthing also in cases of decreased activity of sperms, details of the molecular mechanism behind infertility still remain unclear, and there are many cases leading to difficulties in the selection of proper treatments and also to unsatisfactory therapeutic effects. For infertility therapy with fewer burdens, therefore, there is a strong request for developing genetic diagnoses and assisted reproductive technologies based on the understanding of the mechanism of infertility According to Non Patent Literature 1, studies on male infertility in mice have demonstrated the existence of many genes which affect fertility. Mutations in these genes would be likely to contribute to causing male infertility also in humans.

As concerns morphological changes which are brought about after the meiosis during the process of sperm formation, on the other hand, it is reported that structural or functional changes specific to sperm cells are observed in enzymes utilized in energy metabolism. For example, there is observed activation of sperm-specific hexokinase (see, Non Patent Literature 2), phosphoglucoseisomerase (see, Non Patent Literature 3), aldolase (see, Non Patent Literature 4), glyceroaldehyde 3-phosphate dehydrogenase (see, Non Patent Literature 5), phosphoglycerate kinase (see, Non Patent Literature 6), phosphoglycerate mutase (see, Non Patent Literature 7), enolase (see, Non Patent Literature 8), and others. In Non Patent Literature 5, it is suggested that abnormalities in functions of these sperm-specific glycolytic enzymes is likely to be a cause of infertility, because (male) mice knocked-out for glyceroaldehyde 3-phosphate dehydrogenase are infertile and found to have poor motility of sperm.

Members of the family of phosphoglycerate mutases (PGAMs) in mice are encoded by two genes, Pgam-1 and Pgam-2, and form three isozymes, homo-PGAMs of type B and type M, and a hetero-PGAM. Although isozymes of these three types are detected in the testis of grown mice, type M isozyme is not identified in the testis of newborn mice and observed at 14 to 16 days after birth and later (see, Non Patent Document 9). It has been demonstrated that at the transcription level, type B is expressed strongly in the brain and kidney and moderately in the liver, thyroid gland, muscle, and heart, and type M strongly in the muscle and testis and moderately in the heart and lung (see, Non Patent Document 10). While expression analysis of PGAM in human testis has not been made, it has been found that PGAM1 (type B) is expressed in the liver and brain and PGAM2 (type M) in the muscle (see, Non Patent Document 11). In humans, it is known that as an isozyme of type B, PGAM4 containing no introns (PGAM3, PGAM-B) is present (see, Non Patent Document 12). Functioning of PGAM4 in the testis would be suggested, because PGAM of type M, in addition to type B, is thought to be expressed also in the human matured testis, while many of the genes expressed specifically in the testis do not contain introns (see, Non Patent Documents 13 and 14). Therefore, changes in the gene encoding PGAM4 may lead to abnormalities in PGAM functions in sperms. As a result, it would be likely that the energy supply via the glycolytic system is reduced and the motility of sperm is decreased, thereby resulting in impairments in fertilization

CITATION LIST

Non Patent Literature

[Non Patent Literature 1]
Matzuk and another, Nature Cell Biology, 2002, Vol. 4 (Suppl. 1), S41-S49.
[Non Patent Literature 2]
Mori and four others, Molecular Reproduction and Development, 1996, Vol. 44, No. 1, pp. 14-22.
[Non Patent Literature 3]
Buehr and another, Journal of Reproduction and Fertility, 1981, Vol. 63, No. 1, pp. 169-173.
[Non Patent Literature 4]
Vemuganti and five others, Developmental Biology, 2007, Vol. 309, No. 1, pp. 18-31
[Non Patent Literature 5]
Miki and eight others, Proceedings of the National Academy of Science of the United States of America, 2004, Vol. 101, No. 47, pp. 16501-16506
[Non Patent Literature 6]
McCarrey and six others, Developmental Genetics, 1996, Vol. 19, No. 4, pp. 321-332
[Non Patent Literature 7]
Broceno and four others, European Journal of Biochemistry, 1995, Vol. 227, No. 3, pp. 629-635.
[Non Patent Literature 8]
Force and four others, Journal of Andrology, 2004, Vol. 25, No. 5, pp. 824-829.

[Non Patent Literature 9]
Fundele and four others, Developmental Biology, 1987, Vol. 124, No. 2, pp. 562-566.
[Non Patent Literature 10]
Zhang and eight others, Gene, 2001, Vol. 264, No. 2, pp. 273-279.
[Non Patent Literature 11]
Sakoda and four others, The Journal of Biological Chemistry, 1988, Vol. 263, No. 32, pp. 16899-16905.
[Non Patent Literature 12]
"Symbol Report: PGAM4," [online], Apr. 25, 2005, Human Genome Organization, [searched on Dec. 2, 2008], internet <URL: http://www.genenames.org/data/hgnc_data.php?hgnc_id.21731>.
[Non Patent Literature 13]
McCarrey and another, Nature, 1987, Vol. 326, No. 6112, pp. 501-505.
[Non Patent Literature 14]
Dahl and four others, Genomics, 1990, Vol. 8, No. 2, pp. 225-232.

SUMMARY OF INVENTION

Technical Problems to be Solved by the Invention

Effective genetic testing/diagnosing methods for the diagnosis of male infertility have not yet been established to a satisfactory degree. The causes of male infertility range widely from deficiency of germ cells themselves to sperm fertilization failure. Therefore, in order to establish an effective treatment in response to pathological conditions, there is a request for a method capable of identifying a cause(s) of various pathological conditions.

The present invention has been made so as to solve the above problems and an object of the present invention is to provide a test/diagnosis method for fertility that is capable of estimation of the possibility of leading to pregnancy and identification of a cause of infertility, based on functions of enzymes involved in the energy supply in the movement of sperms.

Means for Solving the Problems

The present inventors have intensively studied so as to achieve the above object. As a result, the sequence of the human PGAM4 gene was analyzed and mutations related to male infertility were found in the human PGAM4 gene, thereby leading to the completion of the invention, on the supposition that since functionally decreasing of testis-specific PGAM4 would result in decreasing the energy supply in the movement of sperms and thus lowering the probability leading to fertilization, the testis-expressed PGAM4 molecule in humans is related to fertility and mutation in the PGAM4 gene causes (or tends to cause) male infertility.

Accordingly, the present invention includes the following:

(1) A test/diagnosis method for fertility, including a detection step of detecting on a biological sample taken from a human body, the presence or absence of a deletion or mutation in the human PGAM4 gene, wherein the detection step detects the presence or absence of a mutation at one or more bases selected from the group consisting of the 75th position base, the 138th position base, and the 539th position base in a translation region of the human PGAM4 gene, when the adenine in the translation initiation codon is set as the 1st position base.

(2) A test/diagnosis method for fertility, wherein the detection step detects the presence or absence a mutation at one or more bases selected from the group consisting of the 75th position base and the 539th position base in a coding region of the human PGAM4 gene.

(3) A polynucleotide consisting of:
(a) a 10-100 consecutive bases sequence within a base sequence represented by SEQ ID No:3, the 101st base of which being substituted to cytosine from guanine, and said consecutive bases containing the 101st base, or
(b) a base sequence complementary to the above base sequence (a).

(4) A polynucleotide characterized by consisting of:
(c) a 10-100 consecutive bases sequence within a base sequence represented by SEQ ID No:5, the 101st base of which being substituted to adenine from guanine, and said consecutive bases containing the 101st base, or
(d) a base sequence complementary to the above base sequence (c).

(5) A polynucleotide consisting of a base sequence homologous to or complementary to a base sequence of 10-100 consecutive bases in which the 75th position base or the 539th position base in the coding region of the human PGAM4 gene in the base sequence represented by SEQ ID No:1 is substituted and which contains the substituted base.

(6) A polynucleotide consisting of the base sequence represented by SEQ ID No:1, said sequence consisting of a base sequence in which the 138th position base is substituted to cytosine.

(7) A polypeptide consisting of an amino acid sequence encoded by the polynucleotide according to the above (5) or (6).

(8) An antibody being capable of binding to a polypeptide consisting of the amino acid sequence encoded by the polynucleotide according to the above (5) and not being capable of binding to a polypeptide consisting of the amino acid sequence represented by SEQ ID NO:2.

(9) A test/diagnosis method for fertility, including a detection step of detecting on a biological sample taken from a human body, the presence or absence of a mutation in the expressed PGAM4 polypeptide, by using the antibody according to the above (8).

(10) A test kit for human fertility, including a reagent for detecting the presence or absence of a deletion or mutation in the human PGAM4 gene.

(11) The test/diagnosis kit for fertility according to the above (10), wherein the reagent for detecting the presence or absence of a deletion or mutation in the human PGAM4 gene allows detecting of the presence or absence of a mutation at one or more bases selected from the group consisting of the 75th position base, the 138th position base, and the 539th position base in the coding region of the human PGAM4 gene.

(12) The test/diagnosis kit for fertility according to claim 11, wherein the reagent is an anti-PGAM4 antibody.

(13) The test kit for fertility according to the above (11), wherein the reagent is a set of primers which allows amplification of a region containing the base of a mutation detection site in the human PGAM4 gene.

Effects of the Invention

The use of the test/diagnosis method and test/diagnosis kit for fertility of the present invention enables one to perform, with high accuracy and with facility, the estimation of the possibility of leading to pregnancy and the identification of a cause of infertility.

DESCRIPTION OF EMBODIMENTS

The test/diagnosis method for fertility according to the present invention includes a detection step of detecting on a biological sample taken from a human body, the presence or absence of a deletion or mutation in the human PGAM4 gene. Deletions and particular base mutations in the human PGAM4 gene have a high correlation with male infertility. Therefore, the estimation of the possibility of leading to pregnancy and the identification of a cause of infertility can be done by taking a biological sample from a subject and examining using the biological sample, whether or not there is a deletion or mutation in the PGAM4 gene of the subject.

SEQ ID NO:1 is a sequence in which the coding region alone is extracted from the base sequence of the transcription product of the wild-type PGAM4 gene registered as the Accession No. NC_000023.9 in GenBank. As shown in SEQ ID NO:1, the wild-type human PGAM4 gene has a coding region of 765 bp. SEQ ID NO:2 depicts a putative amino acid sequence of the wild-type human PGAM4 protein. According to the Human Genome Resources constructed by the human genome project, the human PGAM4 gene is located on the long arm of human chromosome X (Xq13).

The present inventors found patients who have a substituted base in the coding region of the human PGAM4 gene represented by SEQ ID NO:1, among a group consisting of patients with male infertility, based on the result of the investigation described below in the Examples section. In contrast, none of these base substitutions was observed in a group of males who had been confirmed to have fertility.

The above-described substitution mutation taking place in the human PGAM4 gene would result in no expression of normal protein or decreased efficiency of expression. Therefore, it is speculated that substitution mutation in the human PGAM4 gene is likely to lead to infertility due to the decrease in the amount of translation of normal PGAM4 protein.

In the present invention, a mutation means that a base is deleted, substituted, or inserted in the base sequence of a gene. Mutations in the PGAM4 gene which are detected in the detection step of the test/diagnosis method for fertility according to the present invention are ones which have a high correlation with male infertility. In particular, by detecting at least one mutation from among four mutations described below, the human from whom a biological sample used in the detection step was taken can be examined as to whether or not he has fertility, or as to whether or not the cause of infertility is due to a mutation in the PGAM4 gene, in the case where he has already been diagnosed with infertility, and based on the examination result, the physician can made a diagnosis of fertility. Herein, "the Xth position base in the coding region of the PGAM4 gene" means "the Xth position base in the coding region of the human PGAM4 gene, with the adenine in the translation initiation codon being set as the 1st position base."

Mutations having a high correlation with male infertility include a mutation by which the 75th position guanine in the coding region of the PGAM4 gene is substituted to cytosine. This base substitution leads to a change by which cysteine is encoded instead of tryptophan at the 25th position in the putative amino acid sequence.

Also included is a mutation by which the 138th position adenine in the coding region of the PGAM4 gene is substituted to cytosine. The 138th position base encodes arginine at the 46th position in the putative amino acid sequence, but this base substitution does not change the encoded amino acid, which is still arginine.

Also included is a mutation by which the 539th position guanine in the coding region of the PGAM4 gene is substituted to adenine. This base substitution lead to a change by which histidine is encoded instead of arginine at the 180th position in the putative amino acid sequence.

In the test/diagnosis method for fertility according to the present invention, it is preferred to detect especially the 75th position base or the 539th position base in the coding region of the PGAM4 gene, because these bases have a higher correlation with fertility. In the test/diagnosis method for fertility according to the present invention, detection may be made of one mutation or more than one mutation of the above-described mutations.

The test/diagnosis method for fertility according to the present invention employs these single base mutations as a genetic marker of infertility. For example, if none of these base mutations is detected, then it can be inferred that the subject from whom a biological sample used in the detection step was taken is highly likely to have no problem with fertility. It can be also inferred that when the subject has already been diagnosed to be a patient with infertility, the cause of infertility is highly likely to result from other than functional deletion of the PGAM4 gene. If any of the mutations is detected, on the other hand, the subject will be inferred to have a decreased possibility of leading to pregnancy. Therefore, when the subject is a patient with infertility, it can be determined, by using the test/diagnosis method for fertility according to the present invention, that the cause of infertility is highly likely to be functional deletion of the PGAM4 molecule due to the deletion or mutation in the PGAM4 gene. In consequent, the subject can be administered with an appropriate treatment, such as TESE-ICSI (testicular sperm extraction-intracytoplasmic sperm injection), thereby allowing the subject to be cured early. That is, the test method for fertility according to the present invention may be said to be a test method aimed at estimating the possibility of leading to pregnancy and at identifying a cause of infertility, and the results from the method provide important information in making a diagnosis of infertility, so that to the subject can be presented a proper selection from among the currently existing treatments. For this purpose, the fertility testing method according to the present invention or the like can be preferably used in the diagnosis of reduced fertility or of infertility.

Biological samples used in the fertility testing/diagnosing method according to the present invention are not limited particularly, as long as they are samples that are taken from humans and which could be expected to contain nucleic acids or proteins derived from the PGAM4 gene, and may include blood, serum, plasma, mucosa inside of the cheek and others, semen, intratesticular tissues taken from a subject by testicular biopsy (for example, seminiferous tubules), sperm cells, seminal plasma, and others. Herein, a nucleic acid derived from the PGAM4 gene means genomic DNA of the PGAM4 gene, mRNA which is a transcription product of the PGAM4 gene, and others. A protein derived from the PGAM4 gene means a PGAM4 molecule, which is a protein expressed from the PGAM4 gene, a degradation product thereof, and others. Particularly in cases where a protein derived from the PGAM4 gene is a target to be detected, it is preferred to use, as biological samples, semen, intratesticular tissues taken from a subject by testicular biopsy (for example, seminiferous tubules), sperm cells, seminal plasma, and others. The seminal plasma is considered to contain proteins expressed in sperm cells which are released from sperm cells by their breaking, even though it does not contain sperm cells.

A biological sample may be used directly in the detection step by appropriate dilution, or alternatively DNA, such as genomic DNA, which is extracted in advance from the biological sample may be used. In addition, RNA, such as mRNA, may be extracted from the biological sample and then cDNA which is synthesized from the RNA by reverse transcription reaction may be used in the detection step.

In the detection step of the test/diagnosis method for fertility according to the present invention, methods of detecting a deletion or mutation in the human PGAM4 gene are not limited particularly, and use can be made of a variety of known procedures used, for example, in the detection of gene mutations and polymorphisms, such as base sequencing methods based on the Sanger method, Invader method, Taqman probe method, SMMD (simultaneous multiple mutation detection system) method, PCR-RFLP (polymerase chain reaction-restriction fragment length polymorphism) method, MASA method, and base elongation method, as well as modified methods thereof. It is preferable that methods used in the detection step are ones by which detection is performed using a probe or primer which has a base sequence recognizing specifically the mutated site, as in Invader method, Taqman probe method, and the like, because these methods are superior in the sensitivity and accuracy of detection.

Probes and primers for the detection of a deletion or mutation in the human PGAM4 gene can be designed and synthesized in routine procedures, based on base sequences of and around the human PGAM4 gene. Those skilled in the art could readily obtain base sequences of and around the human PGAM4 gene from known databases, such as NCBI Human Genome Resources (http://www.ncbi.nlm.nih.gov/genome/guide/human/).

For example, it is possible that as a primer or the like for detecting the presence or absence of a mutation at the 75th position base in the coding region of the PGAM4 gene using mRNA, cDNA obtained from mRNA by reverse transcription reaction, or genomic DNA, use is made of a polynucleotide consisting of the base sequence represented by SEQ ID NO: 3 in which the 101st base is substituted to cytosine from guanine, and which consists of a base sequence homologous to or complementary to a base sequence of 10-100 consecutive bases containing the 101st base. It is also possible that as a primer or the like for detecting that the gene is a wild type in which no mutation takes place at the 75th position base, use is made of a polynucleotide consisting of the base sequence depicted similarly in SEQ ID NO:3 which consists of the base sequence homologous to or complementary to a base sequence of 10-100 consecutive bases containing the 101st base. Herein, the base sequence represented by SEQ ID NO:3 is a partial base sequence of the PGAM4 gene in which the 101st base corresponds to the 75th position base in the coding region of the PGAM4 gene.

Similarly, it is possible that as a primer or the like for detecting the presence or absence of a mutation at the 539th position base in the coding region of the PGAM4 gene using mRNA, cDNA obtained from mRNA by reverse transcription reaction, or genomic DNA, use is made of a polynucleotide consisting of a base sequence homologous to or complementary to a base sequence of 10-100 consecutive bases in which the 101st base in the base sequence represented by SEQ ID NO:5 is substituted to adenine from guanine, and which contains the 101st base. It is also possible that as a primer or the like for detecting that the gene is a wild type in which no mutation takes place at the 539th position base, use is made of a polynucleotide consisting of a base sequence homologous to or complementary to a base sequence of 10-100 consecutive bases in the base sequence depicted similarly in SEQ ID NO:5 which contains the 101st base. Herein, the base sequence represented by SEQ ID NO:5 is a partial base sequence of the PGAM4 gene in which the 101st base corresponds to the 539th position base in the coding region of the PGAM4 gene.

Similarly, it is possible that as a primer or the like for detecting the presence or absence of a mutation at the 138th position base in the coding region of the PGAM4 gene using mRNA, cDNA obtained from mRNA by reverse transcription reaction, or genomic DNA, use is made of a polynucleotide consisting of a base sequence homologous to or complementary to a base sequence of 10-100 consecutive bases in which the 101st base in the base sequence represented by SEQ ID NO:4 is substituted to cytosine from adenine, and which contains the 101st base. It is also possible that as a primer or the like for detecting that the gene is a wild type in which no mutation takes place at the 138th position base, use is made of a polynucleotide consisting of a base sequence homologous to or complementary to a base sequence of 10-100 consecutive bases in the base sequence depicted similarly in SEQ ID NO:4 which contains the 101st base. Herein, the base sequence represented by SEQ ID NO:4 is a partial base sequence of the PGAM4 gene in which the 101st base corresponds to the 138th position base in the coding region of the PGAM4 gene.

As mentioned above, it is possible that as a primer or the like for detecting the presence or absence of each of the mutations described above, use is made of a polynucleotide consisting of a base sequence homologous to or complementary to a base sequence of 10-100 consecutive bases containing the mutated site in question, in the base sequence of the coding region of the human wild-type PGAM4 gene (the base sequence represented by SEQ ID NO:1), with the adenine of the translation initiation codon being set as the 1st position base. It is also possible to use a polynucleotide consisting of a base sequence homologous to or complementary to a base sequence of 10-100 consecutive bases containing the mutated site in question, in genomic DNA of the human wild-type PGAM4 gene. The length of these polynucleotides is preferably 10-70 bases in length, more preferably 10-50 bases in length, and further preferably 10-30 bases in length. In addition, in order to improve the accuracy of detection of the presence or absence of the mutation, the position within the polynucleotide of a base which can pair to the base of the mutated site is not limited particularly, and is preferably located within 1 to 5 bases from the 3'-end, more preferably at the 3'-end.

The test/diagnosis method for fertility according to the present invention can be more simply carried out by using a kit for testing human fertility, wherein the kit includes a reagent for detecting the presence or absence of a deletion or mutation in the human PGAM4 gene. The test kit for fertility according to the present invention preferably includes a reagent for detecting a mutation at the 75th position base, the 138th position base, or the 539th position base, more preferably at the 75th position base or the 539th position base, in the coding region of the human PGAM4 gene, with the adenine of the translation initiation codon being set as the 1st position base. The kit may include a reagent for detecting one mutation or more than one mutation of these mutations.

Reagents for detecting these base mutations may include, for example, a set of primers for amplifying a nucleic acid region containing the base in question by PCR and others, and a base-sequencing reagent for determining the base sequence of the resulting amplified product. The base-sequencing reagent may include, for example, a hybridization probe in which a polynucleotide is previously labeled with a fluorescent dye or the like, wherein the polynucleotide consists of a base sequence homologous to or complementary to a base sequence of 10-100 consecutive bases which contains the mutated site in the base sequence of the above-mentioned human wild-type PGAM4 gene or of its coding region. In addition, when the method of detecting a deletion or mutation in the human PGAM4 gene is a PCR-RFLP method, a restriction enzyme used in the RFLP method may be used as the detection reagent.

The test/diagnosis method and test kit for fertility according to the present invention are not limited particularly in their aspects, as long as the method and kit detect the presence or absence of a mutation leading to functional deletion of the human PGAM4 gene. For example, the test/diagnosis method and test kit for fertility as described above may detect that the human PGAM4 gene of a subject contains a mutation leading to functional deletion of the gene, or that the human PGAM4 gene of a subject does not contain any mutation leading to functional deletion of the gene.

More specifically, in an embodiment, the test/diagnosis method and test kit for fertility according to the present invention may detect the presence or absence of the above-described substitution mutation by base sequencing a region containing the base of each of the mutated sites described above (hereinafter referred to as "mutation detection sites") among regions within the human PGAM4 gene. Base sequencing can use the Sanger method and various known procedures to which the Sanger method is applied.

In this case, the test kit for fertility may include as a reagent for detecting the presence or absence of a deletion or mutation in the human PGAM4 gene, a set of primers which are designed such that they are located on either side of the mutation detection site, in order to amplify a region containing the above-described mutation detection site of the human PGAM4 gene. More particularly, this set of primers include a first primer and a second primer, wherein the first primer has a part or all of the upstream base sequence of the mutation detection site of the human PGAM4 gene and the second primer has a base sequence complementary to a part or all of the downstream base sequence of the mutation detection site of the human PGAM4 gene.

It is possible to detect reliably and simply the presence or absence of a substitution mutation by performing PCR with the above-described set of primers, using as the template a genomic DNA which is contained in a biological sample taken from a subject, thereby to amplify, as a DNA fragment, a region containing the base of the mutation detection site of the human PGAM4 gene, and further determining its base sequence using one or both of the primers of the above-described primer set. Base sequencing can be done with facility, for example, by using an ABI-PRISM 310 Genetic Analyzer (Applied Biosystems Inc.) or the like following the instructions.

In addition, use may be made of primers other than the primers used in PCR for amplification of DNA fragments, as a primer used for base sequencing. Therefore, the test kit for fertility may include a set of primers for amplifying a DNA fragment, and a primer used for base sequencing, as reagents for detecting the presence or absence of a deletion or mutation in the human PGAM4 gene.

The above-described set of primers for amplification of DNA fragments is such that the length of a region included between the primers is preferably 5 kb or less, more preferably 3 kb or less, further preferably 2 kb or less, and particularly preferably 1.5 kb or less. Reducing the length of a region included between the primers will allow effective amplification of a region containing the base of the above-described mutation detection site.

The primer used for base sequencing is preferably designed so that it is located at a position within 2 kb, preferably within 1.5 kb, more preferably within 1.0 kb, and particularly preferably within 0.7 kb, from the base of the above-described mutation detection site. These settings will allow one to perform base sequencing with accuracy.

Further, the primer used for base sequencing is preferably designed so that it is located at a position of 20 bp or more, more preferably 30 bp or more, further preferably 40 bp or more, and particularly preferably 50 bp or more, away from the base of the above-described mutation detection site. It is preferred that the above-described set of primers amplifies a region of 20 bp or more containing the base of the mutation detection site of the human PGAM4 gene. Although a region in the proximity of the primer tends to give wrong results of base sequencing, these settings will allow one to perform base sequencing with accuracy.

Each of these primers preferably has a base sequence of at least 10 bases or more, more preferably 15 bases or more, further preferably 18 bases or more, and particularly preferably 20 bases or more, which is identical or complementary to or around the PGAM4 gene. Extending of the length of a base sequence identical (or complementary) to or around the PGAM4 gene will allow ensuring that amplification is made of only the target region that contains at least one of the mutated sites of the PGAM4 gene.

As the set of primers as described above can be used a set of a primer consisting of the base sequence represented by SEQ ID NO: 6 and a primer consisting of the base sequence represented by SEQ ID NO:7, although it goes without saying that the base sequence of primers which can be used in the present invention is not limited to these sequences. Those skilled in the art could readily obtain base sequences of and around the human PGAM4 gene from the Human Genome Resources and GenBank as described above, and design primers using Oligo® (National Bioscience Inc.), GENETYX (Software Development Co., Ltd.), or the like, based on the base sequence obtained.

Each of the respective primers can be synthesized by known methods, such as phosphoramidite method, and for example, can be synthesized with facility by using a Model 392 Synthesizer available from Applied Biosystems Inc. or the like following the instructions.

Each of the primers as described above may have a fluorescent label attached thereto. When each of the primers has a fluorescent label attached thereto, the base sequence of an amplified region can be determined by the dye primer method without any radioisotope.

When neither of the primers has a fluorescent label attached thereto, on the other hand, base sequencing can be done by the dye terminator method. In this case, the test kit for fertility as described above may further include, in addition to the above-described set of primers, deoxyribonucleic acids of respective monomers A, T, G, and C, dideoxyribonucleic acids of respective fluorescently-labeled monomers A, T, G, and C (so-called dye terminators), polymerase, and others.

In an embodiment, the test/diagnosis method and test kit for fertility according to the present invention may detect the presence or absence of base substitution mutation at the above-described mutation detection sites of the human PGAM4 gene by the Invader method. The details of the Invader method are described in an article by Lyamichev et al. (Lyamichev V et al., Nat Biotechnol. 17, 292, 1999), which is incorporated herein by reference.

Figure 1:
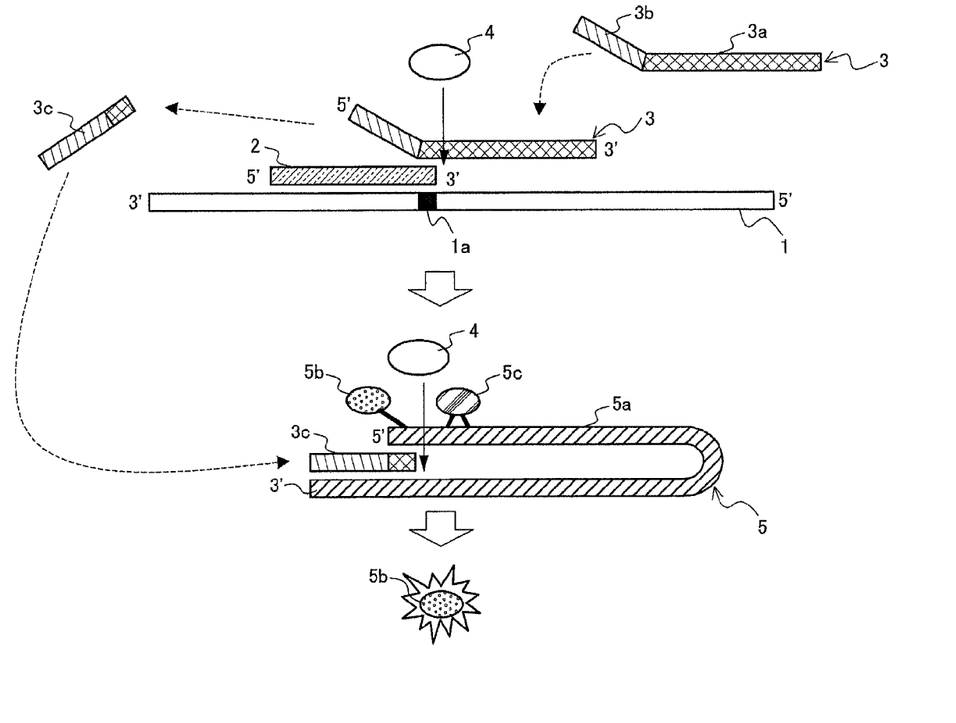
FIG. 1 is a schematic view showing the principle of the Invader method.

FIG. 1 is a schematic illustration explaining the principle of the Invader method. The Invader method uses an Invader oligo 2 and an allele oligo 3, which are non-fluorescently labeled probes, and a FRET probe 5, which is a fluorescently labeled probe.

An Invader probe 2 is designed such that it has a base sequence complementary to a target gene 1 and its 3'-terminal base corresponds to a mutation (or single base polymorphism) detection site 1a of the target gene 1 (and has a base not complementary to any base). An allele oligo 3 has a combination of a flap 3b, which is of a base sequence unrelated to the target gene 1, and a nucleotide 3a, which is designed such that it has a base sequence complementary to the target gene 1 and its 5'-terminal base is complementary to the mutation (or single base polymorphism) detection site 1a of the target gene 1, wherein the flap 3b is joined at the 5'-end of the nucleotide 3a.

When the Invader probe 2 and the allele oligo 3 thus designed are allowed to hybridize to the target gene 1, these are hybridized to the target gene 1 with taking a structure where the allele oligo 3 and the Invader probe 2 are overlapped, so that the Invader probe 2 invades below the allele oligo 3 by only one base at the mutation detection site 1a. In this situation, a flap endonuclease (also referred to as "cleavase") 4 recognizes the invasion structure and cleaves the allele oligo 3 at the 3' side of the overlapped base. As the result, a detached flap 3c in which the flap 3b and the mutation detection site are joined is generated.

A FRET probe 5 consists of a nucleotide 5a of which the 5'-end side is hybridizable to itself and of which the 3'-end side is hybridizable to the flap 3b, a fluorescent dye 5b, and a quencher (light-generation suppressor) 5c, wherein the nucleotide 5a has at its 3' end a base sequence complementary to the detached flap 3c. The fluorescent dye 5b is attached at the 5' end of the nucleotide 5a. In the FRET probe 5, the fluorescence from the fluorescent dye 5b is suppressed by the quencher 5c.

Upon hybridization of the detached flap 3c to the FRET probe 5, an invasion structure is formed again at the mutation detection site of the detached flap 3c. As a result, the above-described flap endonuclease 4 recognizes again this invasion structure and cleaves off the 5'-terminal portion of the FRET probe 5. Consequently, the fluorescent dye 5b which is attached at the 5' end of the FRET probe 5 is released, thereby resulting in generation of the fluorescence.

Therefore, the test/diagnosis method and test kit for fertility according to the present invention may detect the presence or absence of a deletion or mutation in the human PGAM4 gene by the Invader method. In this case, the test kit preferably includes an Invader probe 2, an allele oligo 3, a FRET probe 5, and others, as reagents for detecting the presence or absence of a deletion or mutation in the human PGAM4 gene.

In order that the fluorescence is generated when a substitution mutation is present in the human PGAM4 gene, the Invader probe 2 is designed such that it has a base sequence complementary to the human PGAM4 gene and its 3'-terminal base corresponds to each of the mutated bases of a mutated PGAM4 gene (but is not complementary). The nucleotide 3a of the allele oligo 3 is designed such that it has a base sequence complementary to the human PGAM4 gene and its 5'-terminal base is complementary to the above-described mutated base of the mutated PGAM4 gene. The FRET probe 5 is designed such that detection can be made of the detached flap 3c which has been cleaved off by a flap endonuclease 4 when the Invader probe 2 and the allele oligo 3 hybridizes to the mutated PGAM4 gene, thereby to form an invasion stricture by the Invader probe 2.

Under the above settings, the 3' end of the Invader probe 2 invades beneath the 5' end of the nucleotide 3a which has hybridized to the target gene, whereby the nucleotide 3c is cut out, resulting in generation of the fluorescence, in the case where the above-described base is substituted by mutation in the PGAM4 gene of a subject. On the other hand, in the case where the PGAM4 gene of a subject is a wild type, the invasion structure by the terminal portion of the Invader probe 2 is not formed, and thus the nucleotide 3c is not cut out, resulting in no generation of the fluorescence.

In the example described above, the present invention is constructed such that the fluorescence is generated when the PGAM4 gene of a subject has a substitution mutation. However, the present invention is not limited to this example, and may be constructed such that the fluorescence is generated when the PGAM4 gene of a subject is a wild type or such that the fluorescence is suppressed when the PGAM4 gene of a subject has a substitution mutation, or alternatively modified in various ways, for example, so as to use fluorescent dyes which are different between in the wild type and in a mutated gene.

In the above-described methods, a detailed explanation is provided as to the settings in which the presence or absence of a substitution mutation is determined by examining the sense strand of the PGAM4 gene (the strand having codons encoded thereon). However, it goes without saying that the presence or absence of a substitution mutation can be also determined in a similar way by examining the anti-sense strand.

The test/diagnosis method and test kit for fertility according to the present invention may detect at the protein level the presence or absence of a mutation leading to functional deletion of the human PGAM4 gene. Therefore, the detection method and the fertility testing kit according to the present invention may determine in human whether or not a normal protein of human PGAM4 is expressed, or alternatively whether or not an abnormal protein of human PGAM4 is expressed. Herein, a normal protein refers to the human wild-type PGAM4 polypeptide and means a polypeptide consisting of the amino acid sequence represented by SEQ ID NO:2. An abnormal protein means, for example, a polypeptide which has an amino acid sequence encoded by a polynucleotide having a mutation, such as single base substitution mutation, in the polynucleotide consisting of the base sequence of the coding region of the human wild-type PGAM4 gene and which is different from a polypeptide consisting of the amino acid sequence represented by SEQ ID NO: 2. Specifically, an abnormal protein is a polynucleotide characterized by consisting of a base sequence in which the 75th position base is substituted to cytosine or the 539th position base is substituted to thymine in the polynucleotide consisting of the base sequence of the coding region of the human wild-type PGAM4 gene (the base sequence represented by SEQ ID NO:1), with the adenine in the translation initiation codon being set as the 1st position base.

Methods of detecting whether the human PGAM4 protein contained in a biological sample is a normal or an abnormal protein are not limited particularly. For example, an antibody which recognizes only either a normal protein or an abnormal protein of human PGAM4 can be used to detect whether the human PGAM4 protein contained in a biological sample is a normal or an abnormal protein. An antibody characterized in that it binds to an abnormal protein of human PGAM4 and not to a normal protein of human PGAM4 may be used as a reagent for detecting the presence or absence of a deletion or mutation in the human PGAM4 gene which is included in the test kit for fertility according to the present invention. Such an antibody can be produced by employing an abnormal protein of human PGAM4 as an antigen and selecting an antibody that does not cross-react with a normal protein of human PGAM4 from among polyclonal and monoclonal antibodies generated in routine procedures.

Specifically, such an antibody can be produced by subjecting laboratory animals to immunization treatments employing as an antigen a human mutated PGAM4 polypeptide containing the above-mentioned 75th position or 539th position amino acid substitution mutation or its fragment containing the mutated portion (see, for example, Chow, M. et al., Proc. Natl. Acad. Sci. USA, 82:910-914; Francis, M. J. et al., J. Gen. Virol. 66:2347-2354 (1985)).

In general, animals can be subjected to immunization with a free peptide. Efficient immunization may be achieved by coupling a free peptide to a macromolecular carrier (for example, keyhole limpet hemocyanin (KLH) or tetanus toxoid). For example, peptides containing cysteine can be coupled to carriers by linkers, such as m-maleimidebenzoyl-N-hydroxysuccinimide ester (MBS), whereas other peptides can be coupled to carriers by using more common coupling agents, such as glutaraldehyde.

Animals, such as rabbits, rats, and mice, can be immunized by intraperitoneal and/or intradermal injection of an emulsion including a free peptide or carrier-coupled peptide and a Freund's adjuvant. It is desirable to administer booster injections at intervals of about 2 weeks, in order to obtain a useful titer of anti-peptide antibody to such a degree that the antibody is detectable by ELISA.

Then, an antibody can be obtained by collecting the blood from an immunized animal and extracting an IgG fraction from the serum. The antibody is purified by known techniques, whereby the titer of antibody is increased.

The antibody according to the present invention is one which binds to the above-mentioned human mutated PGAM4 polypeptide and not to the human wild-type PGAM4 polypeptide. Therefore, the antibody according to the present invention can be obtained by selecting an antibody that does not bind to the human wild-type PGAM4 polypeptide, from among antibodies obtained by the above-described procedures. To facilitate the above-described selection, it is desirable to select as an antigen peptide to be injected into animals, an oligopeptide of 10 residues or so consisting of an amino acid sequence of and around the mutated portion of a human mutated PGAM4 polypeptide.

As mentioned above, in an embodiment, the test/diagnosis method and test kit for fertility according to the present invention may determine whether a human mutated PGAM4 protein is expressed in a biological sample taken from a human body, by using an antibody that bind to the human mutated PGAM4 protein encoded by a human mutated PGAM4 gene containing at least one of the 75th position or 539th position base substitution and does not bind to the human wild-type PGAM4 protein.

It is highly suggested that the above-mentioned substitution mutation takes place in the human PGAM4 gene in the case where the expression of a human mutated PGAM4 protein is examined using the antibody described above and it is determined that the human mutated PGAM4 protein is expressed in the subject, and at the same time it can be estimated that the subject has a decreased possibility of leading to pregnancy or a strong possibility of being infertile. Additionally, it can be estimated that when the subject suffers from infertility, the cause of infertility is due to abnormalities in the human PGAM4 gene.

In another embodiment, the detection method and the fertility testing kit according to the present invention may determine whether or not normal human PGAM4 protein is expressed in a human, or may determine the quantity of expression of normal human PGAM4 protein.

More specifically, the detection step of the diagnosis method for fertility according to the present invention may detect whether or not the human wild-type PGAM4 protein is present in a biological sample, by using an antibody characterized in that it binds to the human wild-type PGAM4 protein and not to an abnormal human PGAM4 protein. In addition, use may be made of an antibody characterized in that it binds to the human wild-type PGAM4 protein and not to an abnormal PGAM4 protein (anti-PGAM4 antibody), as a reagent for detecting the presence or absence of a deletion or mutation in the human PGAM4 gene which is included in the diagnosis kit for fertility according to the present invention.

It is suggested that there is a deletion or mutation in the human PGAM4 gene in the case where the presence or absence of or the amount of expression of the human PGAM4 protein is examined using the anti-PGAM4 antibody and it is determined that the human PGAM4 protein is not expressed in the subject or that the amount of expression of the human PGAM4 protein is less than in subjects who have no gene mutation, and at the same time it can be estimated that the subject has a decreased possibility of leading to pregnancy or a strong possibility of being infertile. Additionally, it can be estimated that when the subject suffers from infertility, the cause of infertility is due to the fact that normal human PGAM4 gene is not expressed.

Procedures for detecting the human wild-type or a human mutated PGAM4 protein in a biological sample using an antibody are not limited particularly and may use any known procedures. These procedures may include, for example, Western blotting, ELISA (enzyme-linked immunoabsorbent assay), and others.

In cases where the diagnosis kit for fertility is one suitable for methods for diagnosing fertility using Western blotting or ELISA, the diagnosis kit for fertility may include an anti-globulin antibody labeled with a specific enzyme necessary for color reaction, such as peroxidase, in addition to an anti-human wild-type PGAM4 protein antibody or an anti-human mutated PGAM4 antibody, as a reagent for detecting the presence or absence of a deletion or mutation in the human PGAM4 gene.

EXAMPLES

The present invention will be described in more detail by way of Examples. However, the present invention is not limited to the following Examples and various modifications within the scope of the claims can be made. In other words, the technical scope of the present invention also covers embodiments obtained by combinations of technical means that are modified as appropriate within the scope of the claims.

Example 1

In this Example, the sequence of human PGAM4 gene was analyzed and mutations related to male infertility in the human PGAM4 gene were detected.

[Subjects for Analysis]

Japanese male subjects with non-obstructive infertility (N=383) were divided into subgroups, based on the degree of deficits in spermatogenesis. In these subjects with infertility, 13% were non-obstructive azoospermia, 31% were severe oligozoospermia ($<5 \times 10^6$ cells/mL), and 33% were asthenozoospermia, and the remaining 23% did not exhibit any morphological abnormalities. Upon examination of genetic factors, all of these subjects were of primary idiopathic infertility (Guideline for sperm donation, Fertil Steril, 2004:82 (suppl 1):S9-S12). A control group (N=251) was composed of fathers of children who were borne by pregnant women hospitalized in obstetrician clinics, wherein the fathers were confirmed to be fertile. Informed consent was obtained from all donors as to the use of their samples for genome DNA analysis (Urological Section, Osaka University Hospital).

[Screening for Mutation]

In the following steps, treatments were carried out following routine procedures or the instructions supplied with kits, unless indicated otherwise.

Genome DNA was isolated and purified from a blood or semen sample with protease treatment and phenol extraction (Sambrook J et al., Isolation of DNA from Mammalian Cells, New York: Cold Spring Harbor Press, 1989: pp. 9.16-9.21). Blood-derived genome DNA used a DNA which was amplified using GenomiPhi (GE Healthcare Bioscience).

A DNA containing the coding region encoding for the protein of the PGAM4 gene was amplified using the primer-F and primer-R shown in Table 1, according to the PCR reaction conditions shown in Table 2.

The primer-F is a primer designed such that its 5'-terminal base hybridizes to the 98th position base in the base sequence of the PGAM4 gene, with the adenine in the translation initiation codon being set as the 1st position base. The primer-R is a primer designed such that its 5'-terminal base hybridizes to the 850th position base in the base sequence of the PGAM4 gene, with the adenine in the translation initiation codon being set as the 1st position base.

TABLE 1

| | Sequence 5'-3' |
|---|---|
| Primer F | GAGTGGTTAGGGAATAAGGGTGGG (SEQ. ID. NO: 6) |
| Primer R | AGTGTGACATGTGCAGGTGGGAGG (SEQ. ID. NO: 7) |

TABLE 2

| Primers | Denaturing temp. and time | Annealing temp. and time | Extension temp. and time | cycle number | Product size |
|---|---|---|---|---|---|
| Primer F Primer R | 98° C., 10 sec | 68° C., 30 sec | 72° C., 60 sec | 40 cycle | 948 bp |

The resultant PCR amplified fragment was purified with AMPure (Agencourt Bioscience). Sequencing reaction was performed using the purified PCR-amplified fragment as the template and the primers used in amplifying the amplicon. Specifically, sequencing reaction was carried out using Big-Dye® Terminator V3.1 Cycle Sequencing Kit (Applied Biosystems) and the reaction product which was purified with CleanSEQ (Agencourt Bioscience) was analyzed by an ABI-PRISM 3730 Genetic Analyzer (Applied Biosystems). Results of sequencing in both directions were compared to determine the base sequence.

[Results of Sequence Analysis]

As shown in Table 3, a total of 4 mutations were detected upon analysis of the base sequence of the amplicon amplified with the primers F and R, on each of the subjects with infertility and the subjects confirmed to be fertile.

Among these mutations are two substitution mutations with amino acid changes, of which one mutation was also detected in the subjects confirmed to be fertile, and the remaining one mutation was detected in none of the these subjects. One of the two substitution mutations detected also in the subjects confirmed to be fertile was significantly prevalent in the subjects with infertility.

Among two substitution mutations without amino acid changes, one was also detected in the subjects confirmed to be fertile, and the remaining one in none of the subjects confirmed to be fertile.

These results confirmed that the two substitution mutations detected in none of the subjects confirmed to be fertile and the one substitution mutation significantly prevalent in the subjects with infertility were correlated with fertility. The following explains these three substitution mutations.

TABLE 3

| Position | | | Number (%) of SNP | | P |
|---|---|---|---|---|---|
| Nucleotide | Amino acid | Genotype | Infertile | Proven fertile | value |
| 75 | Trp25 | G/G | 359 (95.5) | 238 (98.8) | |
| | Trp25Cys | C/C | 17 (4.5) | 3 (1.2) | 0.025 |
| 123 | Gly41 | C/C | 380 (99.7) | 249 (99.6) | 0.750 |
| | — | T/T | 1 (0.3) | 1 (0.4) | |
| 138 | Arg46 | A/A | 380 (99.7) | 249 (100) | 0.764 |
| | — | C/C | 1 (0.3) | 0 (0) | |
| 539 | Arg180 | G/G | 382 (99.7) | 251 (100) | 0.418 |
| | Arg180His | A/A | 1 (0.3) | 0 (0) | |

One of the 381 subjects with infertility was found to have in both alleles, a substitution of the 138th position adenine to cytosine in the coding region of the PGAM4 gene. This base substitution does not change the 46th position arginine in the putative amino acid sequence. This substitution mutation was found in none of the 249 subjects confirmed to be fertile.

Seventeen of the 376 subjects with infertility were found to have in both alleles, a substitution of the 75th position guanine to cytosine in the coding region of the PGAM4 gene. This base substitution leads to a change by which cysteine is encoded instead of tryptophan at the 25th position in the putative amino acid sequence. This substitution mutation was found in three of the 241 subjects confirmed to be fertile, who have a substitution of the 75th position guanine to cytosine in both alleles.

Additionally, one of the 383 subjects with infertility was found to have in both alleles, a substitution of the 539th position guanine to adenine in the coding region of the PGAM4 gene. This base substitution leads to a change by which histidine is encoded instead of arginine at the 180th position in the putative amino acid sequence. This substitution mutation was found in none of the 251 subjects confirmed to be fertile.

Among these substitution mutations, especially the substitution mutation at the 75th position base was found to occur at a high rate and to have a high correlation with male infertility.

It was inferred that the subjects who were found to have the above-described substitution mutations would have become affected with infertility due to insufficient functioning of the PGAM4 protein by decreased amounts of translation of normal PGAM4 protein. In this connection, it would be likely that the substitution mutation without any amino acid substitution which was detected in none of the subjects confirmed to be fertile (the 138-position substitution mutation) influences the stability of a transcription product and the efficiency of translation, or is a mutation which is linked to other mutations.

The present study found single base polymorphisms other than the above-described substitution mutations in the PGAM4 gene, but these single base polymorphisms exhibited no significant differences in their patterns between the subjects with infertility and the subjects confirmed to be fertile, and thus were not recognized to particularly influence fertility.

INDUSTRIAL APPLICABILITY

Using the test/diagnosis method for fertility and others according to the present invention allows one to estimate the possibility of leading to human pregnancy and to identify a cause of infertility, and provides tools useful for elucidating phenomena associated with infertility and establishing treatments of infertility, as well as for diagnosis of infertility, thereby making it possible that the present invention is suitably utilized in the fields of pharmacy and medicine. For example, genes responsible for male infertility cases which account for 10% or more of the Japanese male infertility cases could be determined by examining together, in addition to the PGAM4 gene of the present invention, gene mutations and SNPs of genes of known inventions, SCOT-t gene (Japanese Patent No. 4,229,973), PRM2 gene (Japanese Patent No. 4,276,691), TP gene (Japanese Unexamined Patent Application, First Publication No. 2007-089409), Centrin-1 gene (Japanese Unexamined Patent Application, First Publication No. 2008-237114), TSSK gene (Japanese Unexamined Patent Application, First Publication No. 2008-067649), and Meisetz gene (Japanese Unexamined Patent Application, First Publication No. 2009-065882). A cause of infertility of men is known to be sex chromosome abnormalities (Y-chromosome mutations) and their frequency of occurrence is 5 to 10%. In developed countries, testing for sex chromosome abnormalities is routinely done as a causal diagnosis for patients with male infertility. Taking the present circumstances into consideration, kits that incorporates the present invention allow one to identify a gene responsible for 10% or more male infertility cases and can be expected to be routinely utilized as tools useful in clinical situations for purposes of selecting scientific evidence-based treatments of infertility and of counseling patients

REFERENCE SIGNS LIST

1 Target gene
1a Mutation (or single base polymorphism) detection site,
2 Invader oligo
3 Allele oligo
3a Nucleotide
3b Flap
3c Detached flap
4 Flap endonuclease
5 FRET probe
5a Nucleotide
5b Fluorescent dye
5c Quencher (light-generation suppressor)

The invention claimed is:

1. A test method for fertility of a human male subject, comprising:

contacting a biological sample obtained from a human male subject with an oligonucleotide comprising 15 or more consecutive nucleotides of SEQ ID NO: 3, wherein the 15 or more consecutive nucleotides includes position 101 of SEQ ID NO: 3, with the exception that position 101 of SEQ ID NO: 3 is a cytosine nucleotide in place of a guanine nucleotide;

detecting the presence or absence of hybridization of the oligonucleotide to target nucleic acids in the biological sample to thereby detect the presence of a cytosine or guanine nucleotide at the 75th nucleotide position of the translation region of the human PGAM4 gene; and assessing fertility of the human male subject based on the presence or absence of a guanine to cytosine mutation at the 75th nucleotide position of the translation region of the human PGAM4 gene, wherein when a guanine nucleotide is detected at the 75th nucleotide position of the human PGAM4 gene, then it is determined that the human male subject is highly likely to have no problem in fertility, and when a guanine nucleotide is not detected at the 75th nucleotide position of the human PGAM4 gene, then it is determined that the human male subject has an increased likelihood of being infertile, wherein the translation initiation codon, adenine, in the coding region of the human PGAM4 gene is set to be the 1st nucleotide.

2. The test method for fertility of a human male subject according to claim 1, wherein the oligonucleotide is a primer and said position 101 is at the 3' end of the primer.

* * * * *